United States Patent [19]

King

[11] 4,220,150

[45] Sep. 2, 1980

[54] NASAL DUST FILTER

[76] Inventor: John R. King, Rt. 1, Summerhill Rd., Thomasville, Ga. 31792

[21] Appl. No.: 941,954

[22] Filed: Sep. 13, 1978

[51] Int. Cl.[3] ............................................ A61M 15/08

[52] U.S. Cl. ................................................ 128/206.11

[58] Field of Search ............... 128/140 N, 140 R, 198, 128/206, 206.11

[56] References Cited

U.S. PATENT DOCUMENTS

| | | | |
|---|---|---|---|
| 1,579,486 | 4/1926 | Pletcher | 128/198 |
| 2,526,586 | 10/1950 | Shuff | 128/140 N |
| 4,030,491 | 6/1977 | Mattila | 128/140 N |

*Primary Examiner*—Henry J. Recla

[57] ABSTRACT

An improved nasal filter that is adapted to be inserted in the nasal passages of the nose and held therein by a clip applying tension on the septum walls. The filter includes a pair of unbrellalike structured cups each having an open base and covered outer side.

The frame of said filter cups are formed from non-allergenic flexible plastics. From a common center cylinder, flexible limbs protrude radially, horizontal and vertically downward and are joined equally at the base and adhered to a soft flexible circular ring which maintains the round shape. The entire outer frame excluding said ring is clad with a thin porous filtering material suitable for filtering dust particles yet maintaining easy breathing.

Within the common center cylinder is located a receiving round socket aperture which connects onto a round ball formed on the ends of the septum bridge clip. This type of connection allows the filter cup to align itself by tilting into position inside the nasal passages and allows the filter cup to be disposed of when saturated with dust particles.

The said septum bridge is made from hard flat flexible plastics which is contoured to fit around the septum with arms extending upward and parallel bowed inward toward each other applying slight tension on the septum walls then angling outward and upward terminating with a round ball for interlockment within said common center cylinder socket apertures walls.

2 Claims, 4 Drawing Figures

NASAL DUST FILTER

BACKGROUND OF THE INVENTION

This invention relates to a nasal filter. More particular to a filter that conforms to the individual wearer's nasal passages therefore making the filter to be made on a productive basis since one particular size will fit a number of wearer's nasal passages.

The prior art teaches a variety of insertable nasal filters, for example, those disclosed in U.S. Pat. Nos. 1,579,486; 2,426,161; 2,433,565; 2,526,586; 2,535,155; 2,674,245; 2,890,695; 3,463,149; 3,747,597; 4,030,491; and others.

SUMMARY OF THE INVENTION

It is accordingly an object of the instant invention to provide for an improved nasal filter.

It is another object to provide for the same relatively little cost thereby making it generally available.

These and other objects of the invention will become more apparent from the following detailed disclosure and claims and by reference to the accompanying drawings, in which:

DETAILED DISCLOSURE

Figure 1:
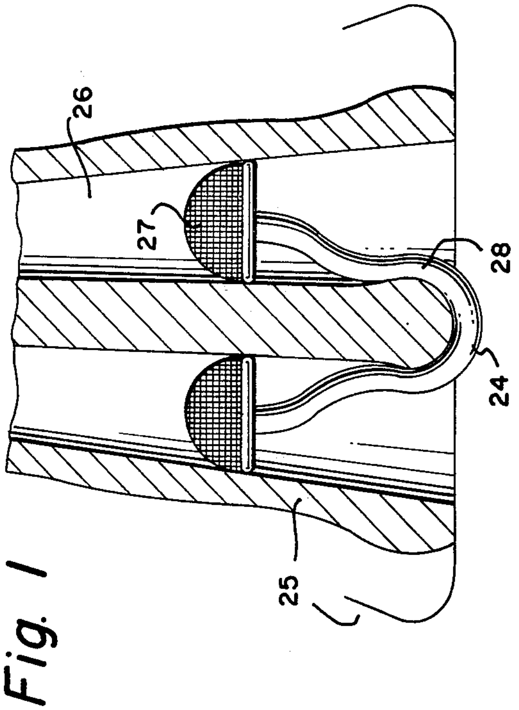
FIG. 1 is a elevational view of the nasal filter showing it in emplacement within the nose of a wearer, the nose being in section.
Figure 3:
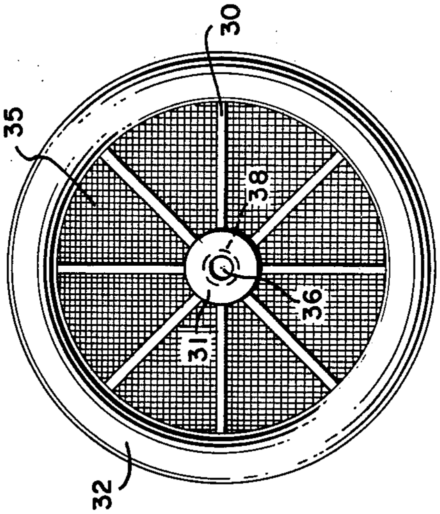
FIG. 3 is a bottom view of the filter.
Figure 2:
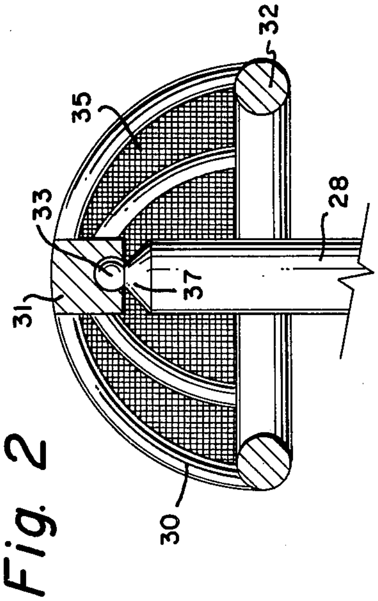
FIG. 2 is a sectional view of one of the filter's mounted on the clip.
Figure 4:
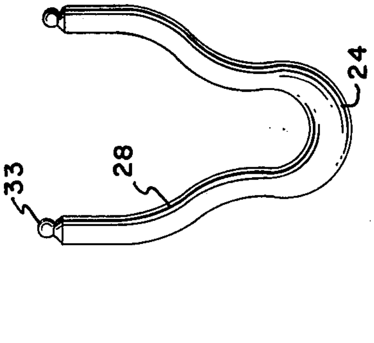
FIG. 4 is a elevational view of the septum bridge clip.

With continuing reference to the accompanying drawings wherein like reference numerals designate similar parts, the umbrellalike filter cups are mounted upon a septum bridge clip 28 which is contoured to fit around the septum walls 25 therefore aligning the filter cups 27 in position within the nasal passages 26. The said septum bridge clip 28 is made from non-allergenic flat surfaced flexible plastics from which a pair of arms extend from a central connecting portion 24 extending vertically upward and parallel around the outer septum 43 then bowed in toward each other to apply slight tension on the septum walls 25 angling at a slight degree upward toward the center of the nasal passages 26 terminating with a round plastic ball 33, for each arm 28.

The filter cups 27 structure is made from non-allergenic flexible plastic materials formed into the shape of an umbrella, open base, covered top. The frame includes a common center socket cylinder, 31 from which flexible plastic limbs 30 protrude horizontally and radially round said cylinder 31 extending vertically downward terminating in equal lengths and adhered by any conventional method to a soft round plastic or rubber ring 32 which maintains the limbs in a desired circular position. The limbs 30 being flexible along with the flexible ring 32 when the filter cup 27 is pushed upward into the nasal passage, position the structure to conform to the individual wearer's nasal passages 26. The limbs 30 excluding the ring 32 are clad over the outside with a thin porous non-allergenic filtering material 35 suitable for breathing easily yet extracting dust particles, and adhered to said limbs by any conventional method. Located at the base of said common center cylinder, a small aperture 36 opens up within the cylinder with a larger aperture cavity 38 large enough to accommodate a round ball 33 located on the clip arms 28. When the ball 33 is pushed through said small aperture 36 into the larger aperture cavity 38 a peripheral ledge 37 captures said ball 33 in place and enables the filter cups 27 to tilt into position inside the nasal passages 26 and enables said filter cups to be disposed of when saturated with dust particles.

I contemplate that changes and modifications may be made in the exact details shown and do not wish to be limited in any particular; rather what I desire to secure and protect by letters Patent of the United States is:

1. A nasal dust filter device adapted to be inserted within the nasal passages of the nose, comprising a pair of umbrellalike structural filter cups, each having an open base and a clad outer side, each open base faces downward, said umbrellalike filter cup structure is formed from non-allergenic flexible plastics, a septum bridge clip formed vertically U-shaped for clipping around the septum with arms formed to apply tension on the septum cartilage walls, said arms extend vertically upward angling at a slight degree outwardly thereby adapted to be positioned toward the center of each nasal passage, said arms each terminating in a round ball, said filter cups including a common center cylinder with plastic limbs protruding radially outward from the top of said common center cylinder both horizontally, vertically and equally downward from the top of said cylinder, said limbs terminate and are adhered to a rubber or flexible plastic ring by any conventional manner, said ring secures said limbs in an umbrellalike shape and enables said limbs and ring to flex and conform to the individual wearer's nasal passages, said limbs are clad over the outside with a thin non-allergenic porous filtering material, said filtering material is adhered to the limbs by any conventional manner suitable, said cylinder extends downwardly from a common center of said limbs and terminates in a horizontally disposed flat base, said base includes a socket aperture cavity comprised of an access aperture followed by an inward larger round cavity to receive said round ball on each arm of said septum clip, each said round ball of said septum clip removably inserted through said access opening and into said larger round cavity, whereby each said round ball is interlocked within said socket aperture cavity which allows each filter cup to be disposed of when saturated with dust particles.

2. The device claimed in claim 1, wherein said filter cup structure includes at least 8 limbs.

* * * * *